US009579066B2

(12) United States Patent
Gottlieb et al.

(10) Patent No.: US 9,579,066 B2
(45) Date of Patent: Feb. 28, 2017

(54) DETERMINATION AND APPLICATION OF GLUCOSE SENSOR RELIABILITY INDICATOR AND/OR METRIC

(71) Applicant: Medtronic MiniMed, Inc., Northridge, CA (US)

(72) Inventors: Rebecca K. Gottlieb, Culver City, CA (US); Ying Luo, Stevenson Ranch, CA (US); Raghavendhar Gautham, Los Angeles, CA (US); Bradley Liang, Bloomfield, MI (US); Anirban Roy, Calabasas, CA (US); Kenneth W. Cooper, Humacao, PR (US); Rajiv Shah, Rancho Palos Verdes, CA (US); Barry Keenan, Hollywood, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 0 days.

(21) Appl. No.: 14/539,855

(22) Filed: Nov. 12, 2014

(65) Prior Publication Data

US 2015/0073244 A1   Mar. 12, 2015

Related U.S. Application Data

(63) Continuation of application No. 13/282,128, filed on Oct. 26, 2011, now Pat. No. 8,919,180.

(60) Provisional application No. 61/407,888, filed on Oct. 28, 2010.

(51) Int. Cl.
*A61B 5/00* (2006.01)
*A61B 5/145* (2006.01)
*A61B 5/1495* (2006.01)
*A61M 5/172* (2006.01)

(52) U.S. Cl.
CPC .......... *A61B 5/7221* (2013.01); *A61B 5/1495* (2013.01); *A61B 5/14503* (2013.01); *A61B 5/14532* (2013.01); *A61B 5/4839* (2013.01); *A61B 5/7275* (2013.01); *A61B 5/743* (2013.01); *A61M 5/1723* (2013.01); *A61M 2005/1726* (2013.01); *A61M 2205/3303* (2013.01); *A61M 2230/201* (2013.01)

(58) Field of Classification Search
CPC .................................. A61B 5/14532
USPC ........ 702/104, 106; 600/316, 319, 347, 365; 73/1.02
See application file for complete search history.

(56) References Cited

U.S. PATENT DOCUMENTS

| | | | |
|---|---|---|---|
| 6,895,263 B2 | 5/2005 | Shin | |
| 7,833,157 B2 | 11/2010 | Gottlieb | |
| 8,657,746 B2 | 2/2014 | Roy | |
| 8,919,180 B2 * | 12/2014 | Gottlieb et al. | ............... 73/1.02 |

(Continued)

OTHER PUBLICATIONS

U.S. Appl. No. 13/282,228, filed Oct. 16, 2011, 75 pages.

(Continued)

*Primary Examiner* — Laura Martin
*Assistant Examiner* — Irving A Campbell
(74) *Attorney, Agent, or Firm* — Berkeley Law & Technology Group, LLP

(57) ABSTRACT

Disclosed are a system and method for determining a metric and/or indicator of a reliability of a blood glucose sensor in providing glucose measurements. In one aspect, the metric and/or indicator may be computed based, at least in part, on an observed trend associated with signals generated by the blood glucose sensor.

23 Claims, 13 Drawing Sheets

(56) References Cited

U.S. PATENT DOCUMENTS

| | | |
|---|---|---|
| 9,033,878 B2 | 5/2015 | Liang |
| 2007/0016381 A1 | 1/2007 | Kamath |
| 2008/0183399 A1 | 7/2008 | Goode |
| 2008/0249384 A1 | 10/2008 | Skyggebjerg |
| 2009/0018418 A1 | 1/2009 | Markle |
| 2009/0156924 A1* | 6/2009 | Shariati et al. ............ 600/365 |
| 2009/0192380 A1 | 7/2009 | Shariati |
| 2010/0094111 A1* | 4/2010 | Heller et al. ............... 600/345 |
| 2010/0162786 A1 | 7/2010 | Keenan |
| 2011/0039295 A1* | 2/2011 | Lok et al. ................... 435/29 |
| 2011/0270346 A1 | 11/2011 | Frei |
| 2011/0313390 A1 | 12/2011 | Roy |
| 2012/0006100 A1 | 1/2012 | Gottlieb |
| 2012/0108932 A1 | 5/2012 | Roy |
| 2012/0108933 A1 | 5/2012 | Liang |

OTHER PUBLICATIONS

U.S. Appl. No. 13/282,228: Filing receipt, mailed Nov. 22, 2011, 3 pages.
U.S. Appl. No. 13/282,228: Notice of publication, mailed May 2, 2012, 1 page.
U.S. Appl. No. 13/282,228: Restriction requirement, mailed Mar. 25, 2014, 6 pages.
U.S. Appl. No. 13/282,228: Restriction requirement response, mailed May 22, 2014, 9 pages.
U.S. Appl. No. 13/282,228: Non-final office action, mailed Jun. 19, 2014, 10 pages.
U.S. Appl. No. 13/282,228: Amendment Req Reconsideration after non final rejection, filed Sep. 19, 2014, 19 pages.
U.S. Appl. No. 13/282,128: Application as filed Oct. 26, 2011, 55 pages.
U.S. Appl. No. 13/282,128: Notice to File Missing Parts, mailed Nov. 8, 2011, 2 pages.
U.S. Appl. No. 13/282,128: Filing Receipt, mailed Nov. 8, 2011.
U.S. Appl. No. 13/282,128: Response to Notice to File Missing Parts, filed Feb. 1, 2011, 11 pages.
U.S. Appl. No. 13/282,128: Filing Receipt, mailed Feb. 10, 2012, 3 pages.
U.S. Appl. No. 13/282,128: Notice of Publication, mailed May 24, 2012, 1 page.
U.S. Appl. No. 13/282,128: Examiner's search strategy and results, mailed Aug. 28, 2013, 5 pages.
U.S. Appl. No. 13/282,128: Non Final Rejection, mailed Aug. 28, 2013, 14 pages.
U.S. Appl. No. 13/282,128: Letter Restarting Period for Response (re References), filed Sep. 10, 2013, 14 pages.
U.S. Appl. No. 13/282,128: Amendment/Req. Reconsideration after non final rejection, filed Dec. 5, 2013, 18 pages.
U.S. Appl. No. 13/282,128: Final Rejection, mailed Mar. 26, 2014, 22 pages.
U.S. Appl. No. 13/282,128: Amendments Arguments Entered with RCE, filed Jun. 12, 2014, 19 pages.
U.S. Appl. No. 13/282,128: Notice of Allowance and Fees, filed Aug. 13, 2014, 8 pages.
U.S. Appl. No. 13/282,128: Amendment after Notice of Allowance (Rule 312), filed Nov. 11, 2014, 7 pages.
U.S. Appl. No. 13/282,128: Issue Fee payment, filed Nov. 11, 2014, 1 page.
U.S. Appl. No. 13/282,128: Amendment After Final, mailed Nov. 21, 2014, 1 page.
U.S. Appl. No. 13/282,128: Response to Amendment after Rule 312, filed Nov. 21, 2014, 2 pages.
U.S. Appl. No. 13/282,128: Issue Notification, mailed Dec. 10, 2014, 1 page.
U.S. Appl. No. 14/686,653, filed Apr. 14, 2015, 80 pages.
U.S. Appl. No. 14/686,653: Filing Receipt, mailed Apr. 27, 2015, 3 pages.
U.S. Appl. No. 14/686,653: Notice to File Corrected Application Papers, mailed Apr. 27, 2015, 3 pages.
U.S. Appl. No. 14/686,653: Applicant Response to Pre-Exam Formalities Notice and Amendment, filed May 14, 2015, 10 pages.
U.S. Appl. No. 14/686,653: Notice of Incomplete Reply, mailed May 28, 2015, 4 pages.
U.S. Appl. No. 14/686,653: Applicant Response to Pre-Exam Formalities Notice and Amendments, filed Jun. 12, 2015, 11 pages.
U.S. Appl. No. 14/686,653: Filing Receipt, mailed Jun. 22, 2015, 3 pages.
Savitzky, A; Golay, MJE: Smoothing and differentiation of data by simplified least squares procedures, Analytical Chemistry 1964, 36(8): 1627-1639.
Jauberteau, F; Jauberteau, JL: Numerical differentiation with noisy signal, Applied Mathematics and Computation 2009; 215: 2283-2297.
Van Den Berghe, Greet, et al., "Intensive Insulin Therapy in Critically Ill Patients" The New England Journal of Medicine, vol. 345, No. 19, Nov. 8, 2001, pp. 1359-1367.
U.S. Appl. No. 14/686,653: Notice of Publication, Oct. 1, 2015, 1 page.

* cited by examiner

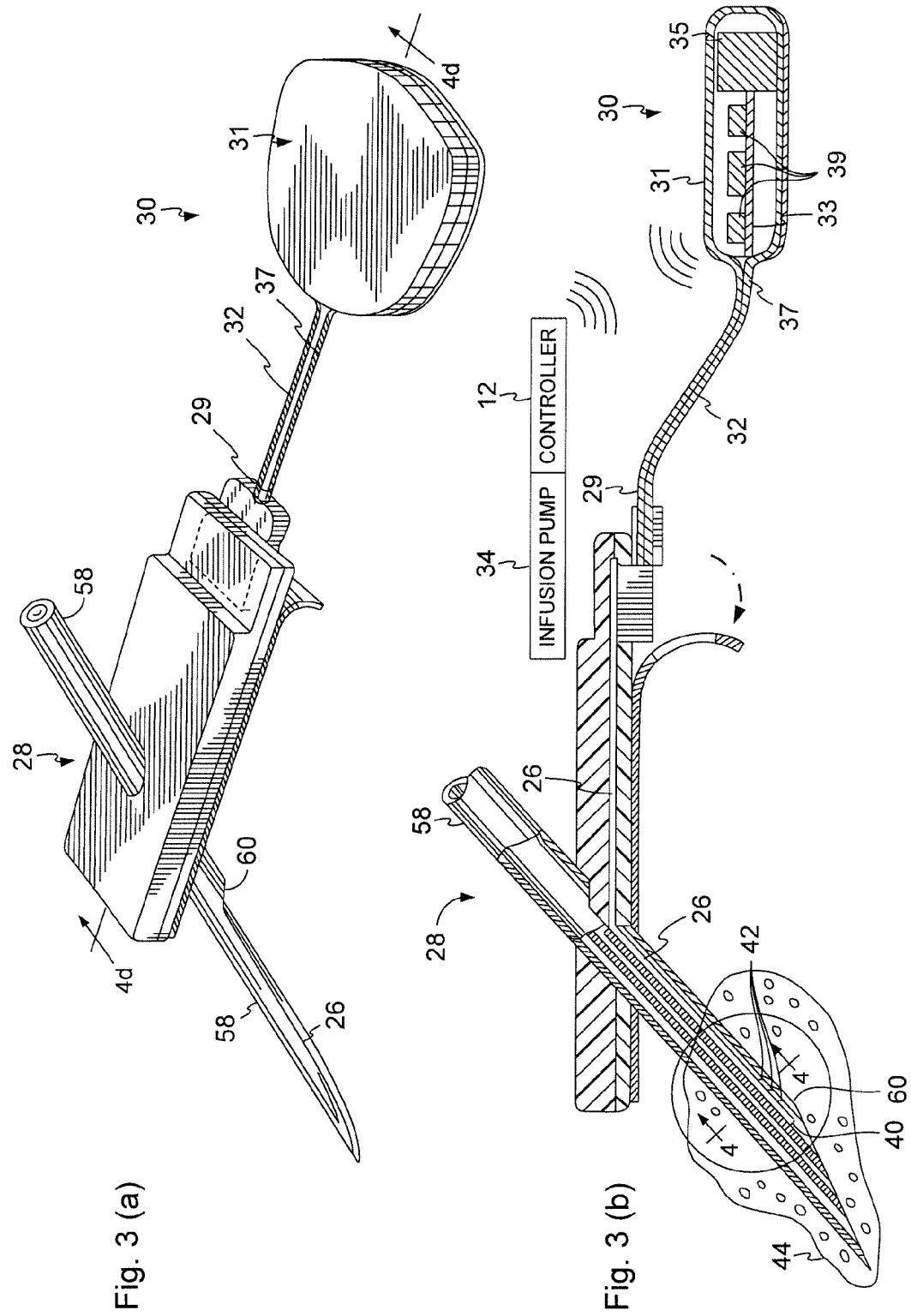

ific implementation, a
DETERMINATION AND APPLICATION OF GLUCOSE SENSOR RELIABILITY INDICATOR AND/OR METRIC This application is a continuation of U.S. patent application Ser. No. 13/282,128, filed on Oct. 26, 2011 and titled "Determination and Application of Glucose Sensor Reliability Indicator and/or Metric," which claims the benefit of U.S. Provisional Patent Application Ser. No. 61/407,888, filed on Oct. 28, 2010, which are assigned to the assignee of claimed subject matter and incorporated herein by reference in their entirety.

BACKGROUND

1. Field

Subject matter disclosed herein relates to glucose sensor signal reliability analysis and application.

2. Information

The pancreas of a normal healthy person produces and releases insulin into the blood stream in response to elevated blood plasma glucose levels. Beta cells (β-cells), which reside in the pancreas, produce and secrete insulin into the blood stream as it is needed. If β-cells become incapacitated or die, which is a condition known as Type I diabetes mellitus (or in some cases, if β-cells produce insufficient quantities of insulin, a condition known as Type II diabetes), then insulin may be provided to a body from another source to maintain life or health.

Traditionally, because insulin cannot be taken orally, insulin has been injected with a syringe. More recently, the use of infusion pump therapy has been increasing in a number of medical situations, including for delivering insulin to diabetic individuals. For example, external infusion pumps may be worn on a belt, in a pocket, or the like, and they can deliver insulin into a body via an infusion tube with a percutaneous needle or a cannula placed in subcutaneous tissue.

As of 1995, less than 5% of the Type I diabetic individuals in the United States were using infusion pump therapy. Over time, greater than 7% of the more than 900,000 Type I diabetic individuals in the U.S. began using infusion pump therapy. The percentage of Type I diabetic individuals that use an infusion pump is now growing at a rate of over 2% each year. Moreover, the number of Type II diabetic individuals is growing at 3% or more per year, and increasing numbers of insulin-using Type II diabetic individuals are also adopting infusion pumps. Physicians have recognized that continuous infusion can provide greater control of a diabetic individual's condition, so they are increasingly prescribing it for patients.

A closed-loop infusion pump system may include an infusion pump that is automatically and/or semi-automatically controlled to infuse insulin into a patient. The infusion of insulin may be controlled to occur at times and/or in amounts that are based, for example, on blood glucose measurements obtained from an embedded blood-glucose sensor, e.g., in real-time. Closed-loop infusion pump systems may also employ the delivery of glucagon, in addition to the delivery of insulin, for controlling blood-glucose and/or insulin levels of a patient (e.g., in a hypoglycemic context). Glucagon delivery may also be based, for example, on blood glucose measurements that are obtained from an embedded blood-glucose sensor, e.g., in real-time.

SUMMARY

Briefly, example embodiments may relate to methods, systems, apparatuses, and/or articles, for monitoring reliability of a sensor. In one particular implementation, a method comprises: determining a metric and/or indicator of a reliability of a blood glucose sensor in providing blood glucose measurements based, at least in part, on an observed trend associated with the blood glucose sensor. In a particular implementation, information may be presented on a display based, at least in part, on the metric and/or indicator. In another particular implementation, an indicator for indicating replacement of the blood glucose sensor based, at least in part, on the metric and/or indicator. In yet another implementation, the blood glucose sensor is coupled to an insulin pump as part of a system to provide closed-loop continuous insulin infusion to a patient, and the method further comprises transitioning the system from closed loop operation to an open loop and/or manual operation based, at least in part, on said metric and/or indicator. In yet another implementation, the method further comprises displaying an indicator requesting additional or more frequent metered blood glucose reference samples for calibration of the sensor in response to the metric and/or indicator to thereby extend an operating life of the blood glucose sensor. In yet another implementation, the observed trend comprises detection of a reduced sensitivity of the sensor in responding to a presence of glucose. In yet another implementation, the observed trend comprises one or more detected non-physiological anomalies. In yet another implementation, the observed trend comprises a sensor drift. The observed trend comprises a noise trend. In yet another implementation, the metric and/or indicator is further based, at least in part, on an indicator of a reliability of a calibration of said blood glucose sensor. In yet another implementation, the blood glucose sensor comprises a plurality of sensor elements, and the method further comprises: combining measurements obtained from the plurality of sensor elements to provide a single measurement of a blood glucose concentration. For example, the metric and/or indicator may be further based, at least in part, on a correlation between output signals of at least two of the plurality of sensor elements.

In another particular implementation, an apparatus comprises: a blood glucose sensor to generate signals responsive to a concentration of glucose in a fluid; and a processor to: determine a metric and/or indicator of a reliability of the blood glucose sensor in providing blood glucose measurements from said signals based, at least in part, on an observed trend associated with said blood glucose sensor. In another example implementation, the blood glucose sensor comprises a plurality of sensor elements, and wherein said processor is further to: combine measurements obtained from the plurality of sensor elements to provide a single measurement of a blood glucose concentration. In yet another implementation, the metric and/or indicator is further based, at least in part, on a correlation between or among output signals of at least two of said plurality of sensor elements.

In another particular implementation, an article comprises: a non-transitory storage medium comprising machine-readable instructions stored thereon which are executable by a special purpose computing apparatus to: determine a metric and/or indicator of a reliability of the blood glucose sensor in providing blood glucose measurements from said signals based, at least in part, on an observed trend associated with the blood glucose sensor. In one particular implementation, the observed trend comprises detection of a reduced sensitivity of the sensor in responding to a presence of glucose. In another particular implementation, the observed trend comprises one or more detected non-physiological anomalies. In yet another particular implementation, the observed trend comprises a sensor drift. In yet another particular implementation, the observed trend comprises a noise trend.

In another particular implementation, an apparatus comprises: means for obtaining signals generated by a blood glucose sensor in response to a presence of glucose in a fluid; and means for determining a metric and/or indicator of a reliability of the blood glucose sensor in providing blood glucose measurements based, at least in part, on an observed trend associated with said obtained signals.

Other alternative example embodiments are described herein and/or illustrated in the accompanying Drawings. Additionally, particular example embodiments may be directed to an article comprising a storage medium including machine-readable instructions stored thereon which, if executed by a special purpose computing device and/or processor, may be directed to enable the special purpose computing device/processor to execute at least a portion of described method(s) according to one or more particular implementations. In other particular example embodiments, a sensor may be adapted to generate one or more signals responsive to a measured blood glucose concentration in a body while a special purpose computing device/processor may be adapted to perform at least a portion of described method(s) according to one or more particular implementations based upon one or more signals generated by the sensor.

BRIEF DESCRIPTION OF THE FIGURES

Non-limiting and non-exhaustive features are described with reference to the following figures, wherein like reference numerals refer to like and/or analogous parts throughout the various figures.

DETAILED DESCRIPTION

Figure 1:
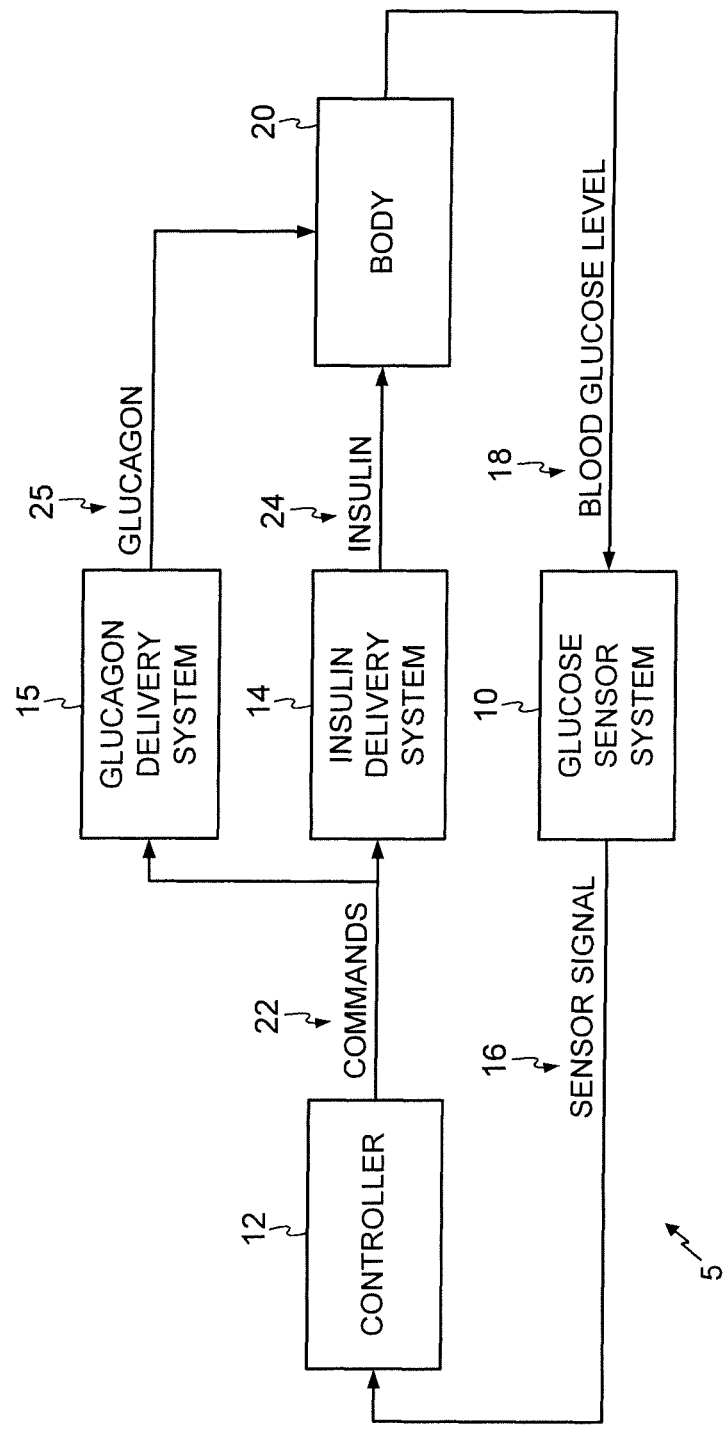
FIG. 1 is a schematic diagram of an example closed loop glucose control system in accordance with an embodiment.

In an example glucose monitoring sensor and/or insulin delivery system environment, measurements reflecting blood-glucose levels may be employed in a closed loop infusion system for regulating a rate of fluid infusion into a body. In particular example embodiments, a sensor and/or system may be adapted to regulate a rate of insulin and/or glucagon infusion into a body of a patient based, at least in part, on a glucose concentration measurement taken from a body (e.g., from a blood-glucose sensor, including a current sensor). In certain example implementations, such a system may be designed to model a pancreatic beta cell (β-cell). Here, such a system may control an infusion device to release insulin into a body of a patient in an at least approximately similar concentration profile as might be created by fully functioning human β-cells, if such were responding to changes in blood glucose concentrations in the body. Thus, such a closed loop infusion system may simulate a body's natural insulin response to blood glucose levels. Moreover, it may not only make efficient use of insulin, but it may also account for other bodily functions as well because insulin can have both metabolic and mitogenic effects.

According to certain embodiments, examples of closed-loop systems as described herein may be implemented in a hospital environment to monitor and/or control levels of glucose and/or insulin in a patient. Here, as part of a hospital or other medical facility procedure, a caretaker or attendant may be tasked with interacting with a closed-loop system to, for example: enter blood-glucose reference measurement samples into control equipment to calibrate blood glucose measurements obtained from blood-glucose sensors, make manual adjustments to devices, and/or make changes to therapies, just to name a few examples. Alternatively, according to certain embodiments, examples of closed-loop systems as described herein may be implemented in non-hospital environments to monitor and/or control levels of glucose and/or insulin in a patient. Here, a patient or other non-medical professional may be involved in interacting with a closed-loop system.

However, while a closed-loop glucose control system is active, oversight by medical professionals, patients, non-medical professionals, etc. may be reduced. Such a closed-loop glucose control system may become at least partially responsible for the health, and possibly the survival, of a diabetic patient. To more accurately control blood glucose levels of a patient, a closed-loop system may be provided with observations or estimates of a current blood glucose level. One approach to providing such observations or estimates is implementation of a blood glucose sensor, such as including one or more such glucose sensors in a closed-loop system.

A closed-loop system may receive at least one glucose sensor signal from one or more glucose sensors, with the glucose sensor signal intended to accurately represent a current (or at least relatively current) blood glucose level. If a glucose sensor signal indicates that a blood glucose level is currently too high, then a closed-loop system may take action(s) to lower the blood glucose level. On the other hand, if a glucose sensor signal indicates that blood glucose level is currently too low, then a closed-loop system may take action(s) to raise the blood glucose level. Actions taken by a closed-loop system to control blood glucose levels of a patient and protect the patient's health may therefore be based at least partly on a glucose sensor signal received from a glucose sensor.

Unfortunately, a received glucose sensor signal may not be completely reliable as a representation of a current blood glucose level of a patient. For example, a received signal may include impurities that obscure a blood glucose level that actually exists in a body currently. By way of example but not limitation, impurities may be introduced if a sensor measures an incorrect blood glucose level (e.g., due to localized pressure at a sensor site, due to improper sensor hydration, due to inflammatory response, etc.), if noise or other factors impact a blood glucose level signal after measurement, combinations thereof, and so forth. Alternatively and/or additionally, a glucose sensor may gradually become increasingly less reliable or capable of accurately measuring a current blood glucose level. In such situations, a glucose sensor signal that is received at a controller of a closed-loop system may not be sufficiently reliable to justify entrusting a patient's life and health to its control decisions.

In certain embodiments that are described herein, a metric and/or indicator may be generated to represent an assessed reliability of a blood-glucose sensor in its ability to provide signal values that accurately reflect a blood-glucose concentration in a patient. Such a metric and/or indicator may be determined using any one of several techniques as discussed below. Additionally as discussed below, such a metric and/or indicator may be determined in connection with a single sensor element obtaining measurements of blood-glucose concentration or multiple sensor elements obtaining such measurements. It should be understood, however, that specific examples of blood-glucose sensors provided herein are merely examples, and that particular techniques to derive a metric and/or indicator representing an ability to provide accurate measurements of a blood-glucose concentration in a patient is not limited to any particular sensor system. Also, as elaborated below, such a metric and/or indicator may be used in any one of several applications to enhance the effectiveness or usefulness of a blood glucose sensor.

FIG. 1 is a block diagram of an example closed loop glucose control system 5 in accordance with an embodiment. Particular embodiments may include a glucose sensor system 10, a controller 12, an insulin delivery system 14, and a glucagon delivery system 15, etc. as shown in FIG. 1. In certain example embodiments, glucose sensor system 10 may generate a sensor signal 16 representative of blood glucose levels 18 in body 20, and glucose sensor system 10 may provide sensor signal 16 to controller 12. Controller 12 may receive sensor signal 16 and generate commands 22 that are communicated at least to insulin delivery system 14 and/or glucagon delivery system 15. Insulin delivery system 14 may receive commands 22 and infuse insulin 24 into body 20 in response to commands 22. Likewise, glucagon delivery system 15 may receive commands 22 from controller 12 and infuse glucagon 25 into body 20 in response to commands 22.

Glucose sensor system 10 may include, by way of example but not limitation, a glucose sensor; sensor electrical components to provide power to a glucose sensor and to generate sensor signal 16; a sensor communication system to carry sensor signal 16 to controller 12; a sensor system housing for holding, covering, and/or containing electrical components and a sensor communication system; any combination thereof; and so forth.

Figure 9:
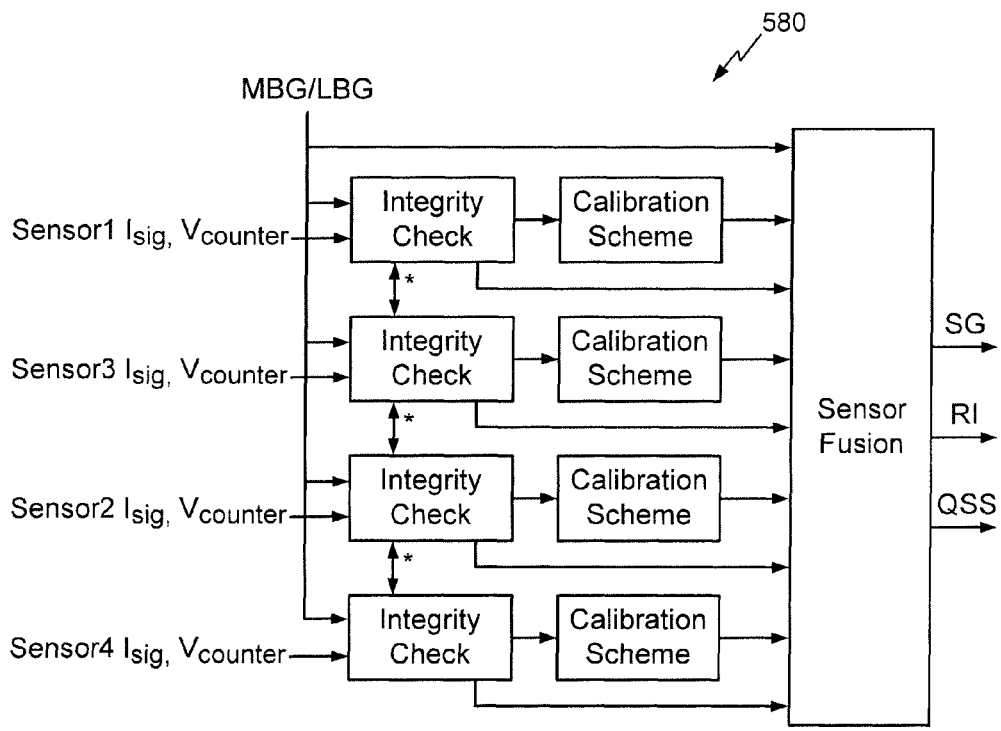

Controller 12 may include, by way of example but not limitation, electrical components, other hardware, firmware, and/or software, etc. to generate commands 22 for insulin delivery system 14 and/or glucagon delivery system 15 based at least partly on sensor signal 16. Controller 12 may also include a controller communication system to receive sensor signal 16 and/or to provide commands 22 to insulin delivery system 14 and/or glucagon delivery system 15. In particular example implementations, controller 12 may include a user interface and/or operator interface (e.g., a human interface as shown in FIG. 9) comprising a data input device and/or a data output device. Such a data output device may, for example, generate signals to initiate an alarm and/or include a display or printer for showing a status of controller 12 and/or a patient's vital indicators, monitored historical data, combinations thereof, and so forth. Such a data input device may comprise dials, buttons, pointing devices, manual switches, alphanumeric keys, a touch-sensitive display, combinations thereof, and/or the like for receiving user and/or operator inputs. It should be understood, however, that these are merely examples of input and output devices that may be a part of an operator and/or user interface and that claimed subject matter is not limited in these respects.

Insulin delivery system 14 may include an infusion device and/or an infusion tube to infuse insulin 24 into body 20. Similarly, glucagon delivery system 15 may include an infusion device and/or an infusion tube to infuse glucagon 25 into body 20. In alternative embodiments, insulin 24 and glucagon 25 may be infused into body 20 using a shared infusion tube. In other alternative embodiments, insulin 24 and/or glucagon 25 may be infused using an intravenous system for providing fluids to a patient (e.g., in a hospital or other medical environment). When an intravenous system is employed, glucose may be infused directly into a bloodstream of a body instead of or in addition to infusing glucagon into interstitial tissue. It should also be understood that certain example embodiments for closed loop glucose control system 5 may include an insulin delivery system 14 without a glucagon delivery system 15 (or vice versa).

In particular example embodiments, an infusion device (not explicitly identified in FIG. 1) may include infusion electrical components to activate an infusion motor according to commands 22; an infusion communication system to receive commands 22 from controller 12; an infusion device housing (not shown) to hold, cover, and/or contain the infusion device; any combination thereof; and so forth.

In particular example embodiments, controller 12 may be housed in an infusion device housing, and an infusion communication system may comprise an electrical trace or a wire that carries commands 22 from controller 12 to an infusion device. In alternative embodiments, controller 12 may be housed in a sensor system housing, and a sensor communication system may comprise an electrical trace or a wire that carries sensor signal 16 from sensor electrical components to controller electrical components. In other alternative embodiments, controller 12 may have its own housing or may be included in a supplemental device. In yet other alternative embodiments, controller 12 may be co-located with an infusion device and a sensor system within one shared housing. In further alternative embodiments, a sensor, a controller, and/or infusion communication systems may utilize a cable; a wire; a fiber optic line; RF, IR, or ultrasonic transmitters and receivers; combinations thereof; and/or the like instead of electrical traces, just to name a few examples.

Figure 2:
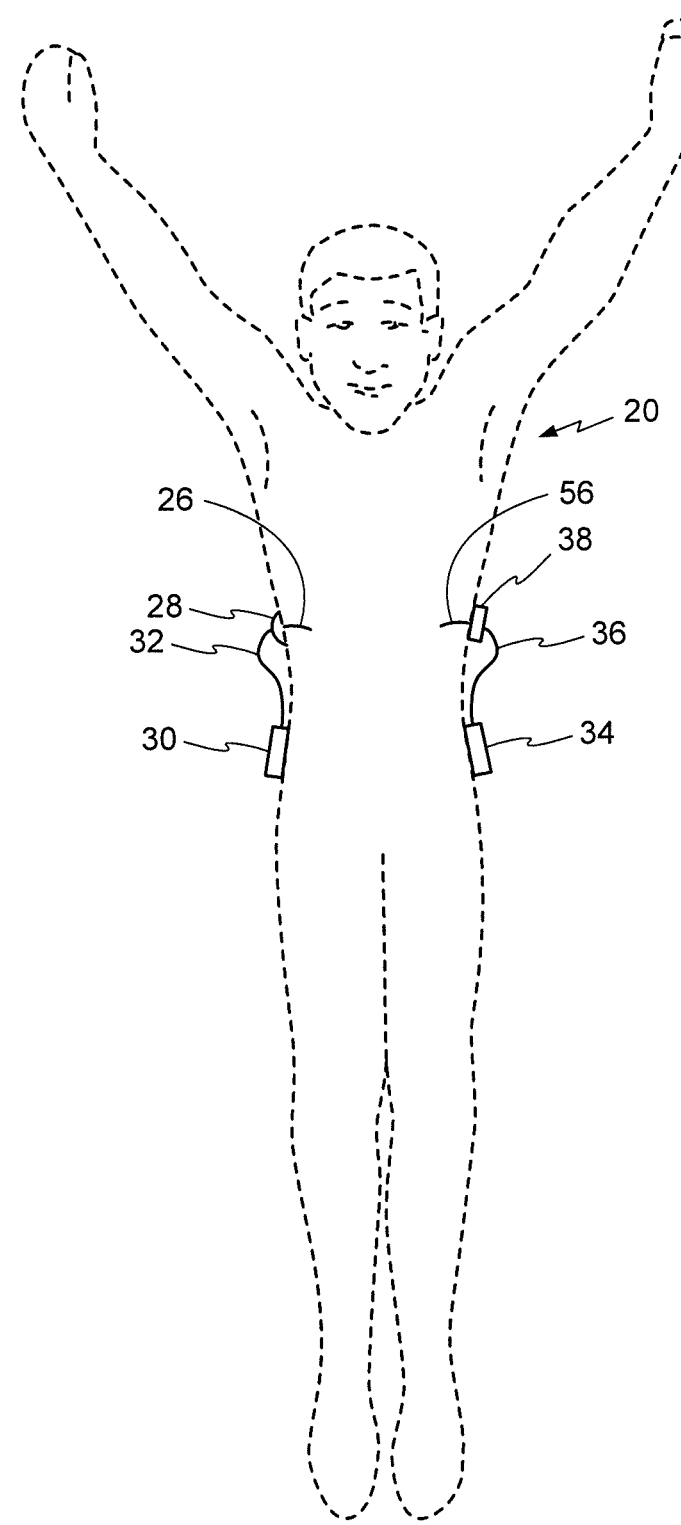
FIG. 2 is a front view of example closed loop hardware located on a body in accordance with an embodiment.
Figure 3:
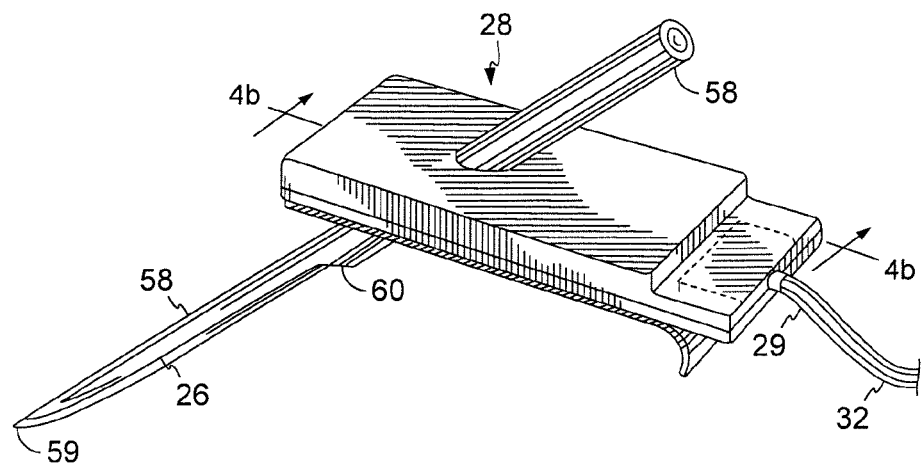
FIG. 3(a) is a perspective view of an example glucose sensor system for use in accordance with an embodiment.
FIG. 3(b) is a side cross-sectional view of a glucose sensor system of FIG. 3(a) for an embodiment.
FIG. 3(c) is a perspective view of an example sensor set for a glucose sensor system of FIG. 3(a) for use in accordance with an embodiment.
FIG. 3(d) is a side cross-sectional view of a sensor set of FIG. 3(c) for an embodiment.
Figure 3:
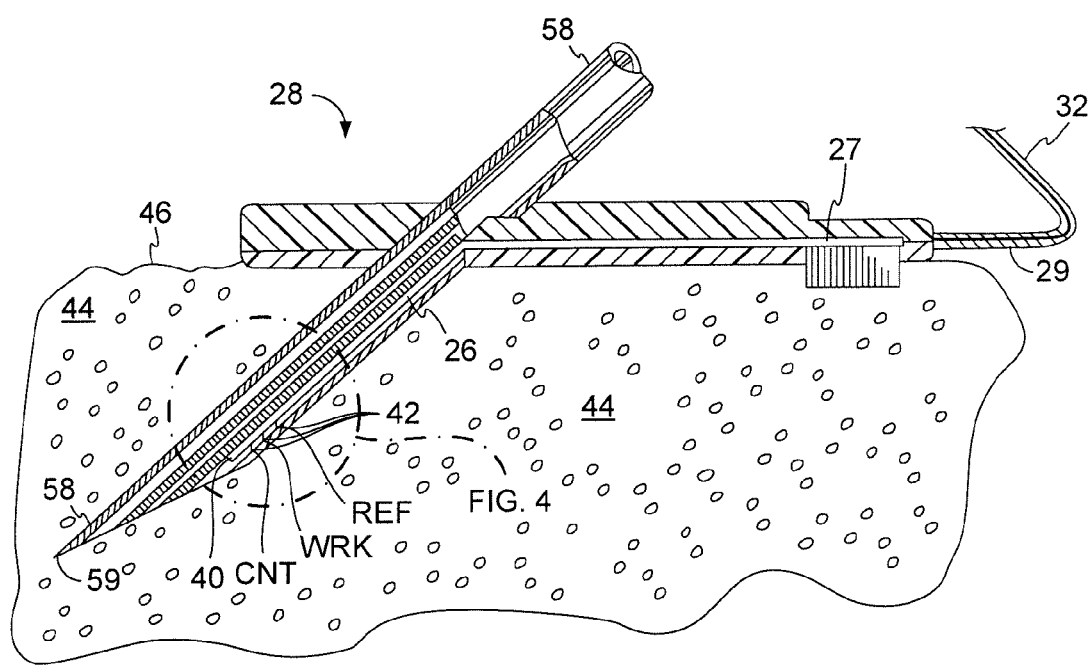
Figure 4:
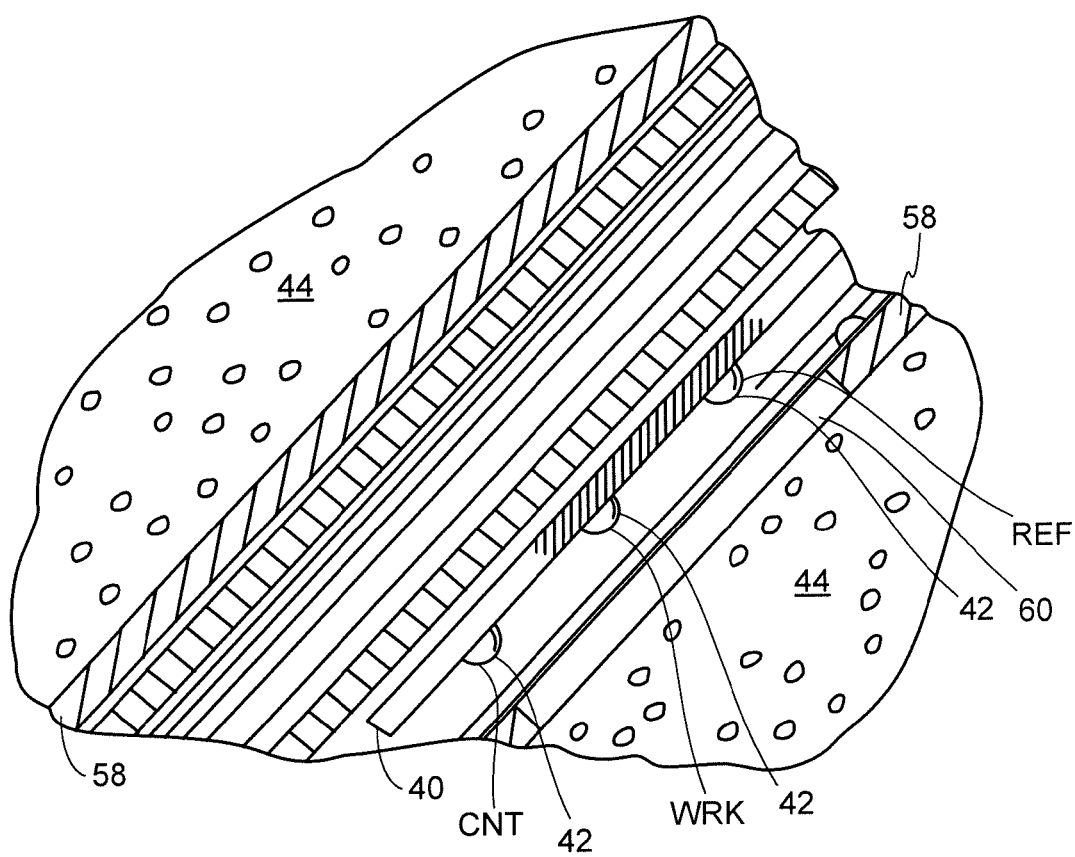
FIG. 4 is a cross sectional view of an example sensing end of a sensor set of FIG. 3(d) for use in accordance with an embodiment.
Figure 5:
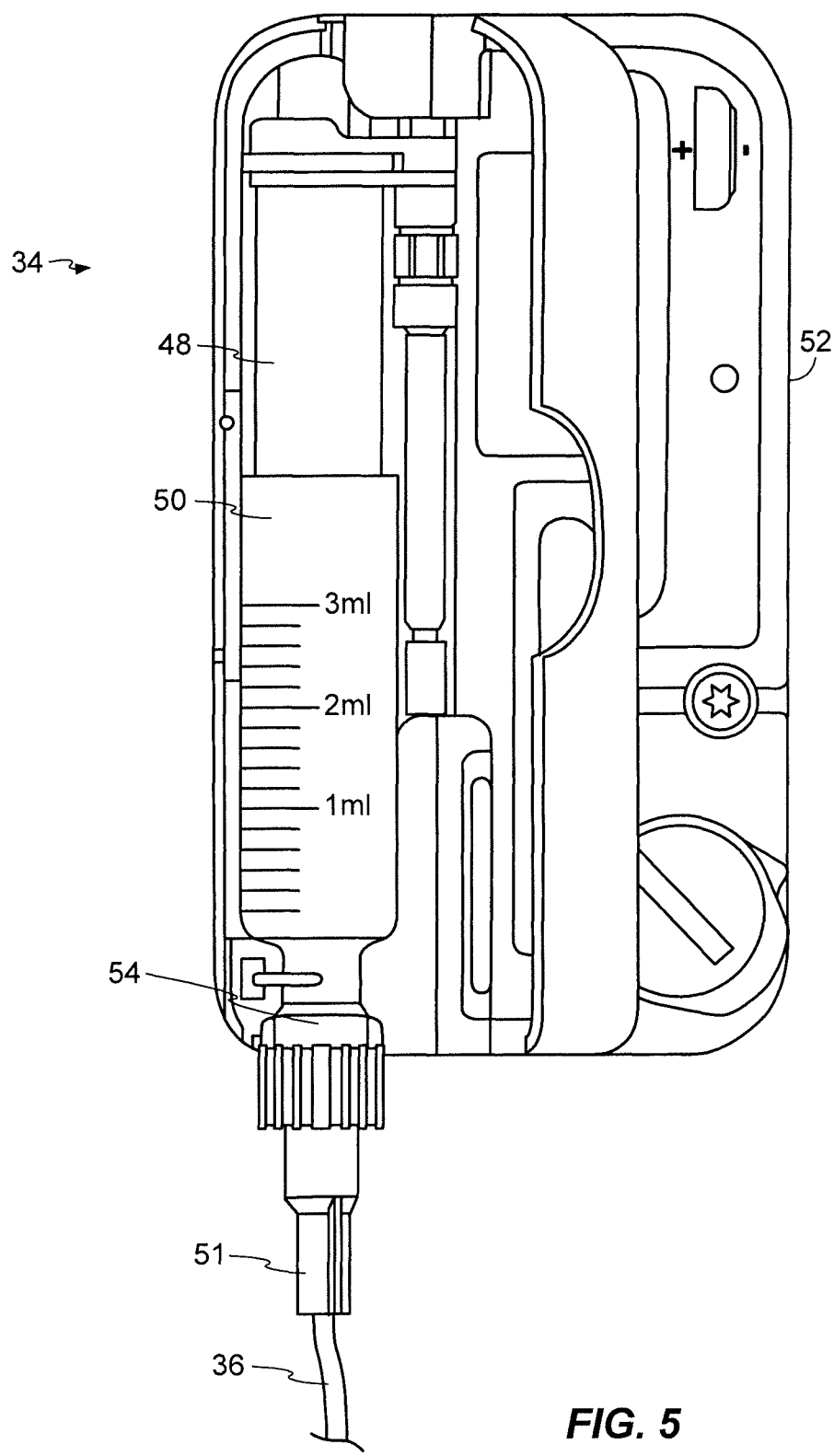
FIG. 5 is a top view of an example infusion device with a reservoir door in an open position, for use according to an embodiment.
Figure 6:
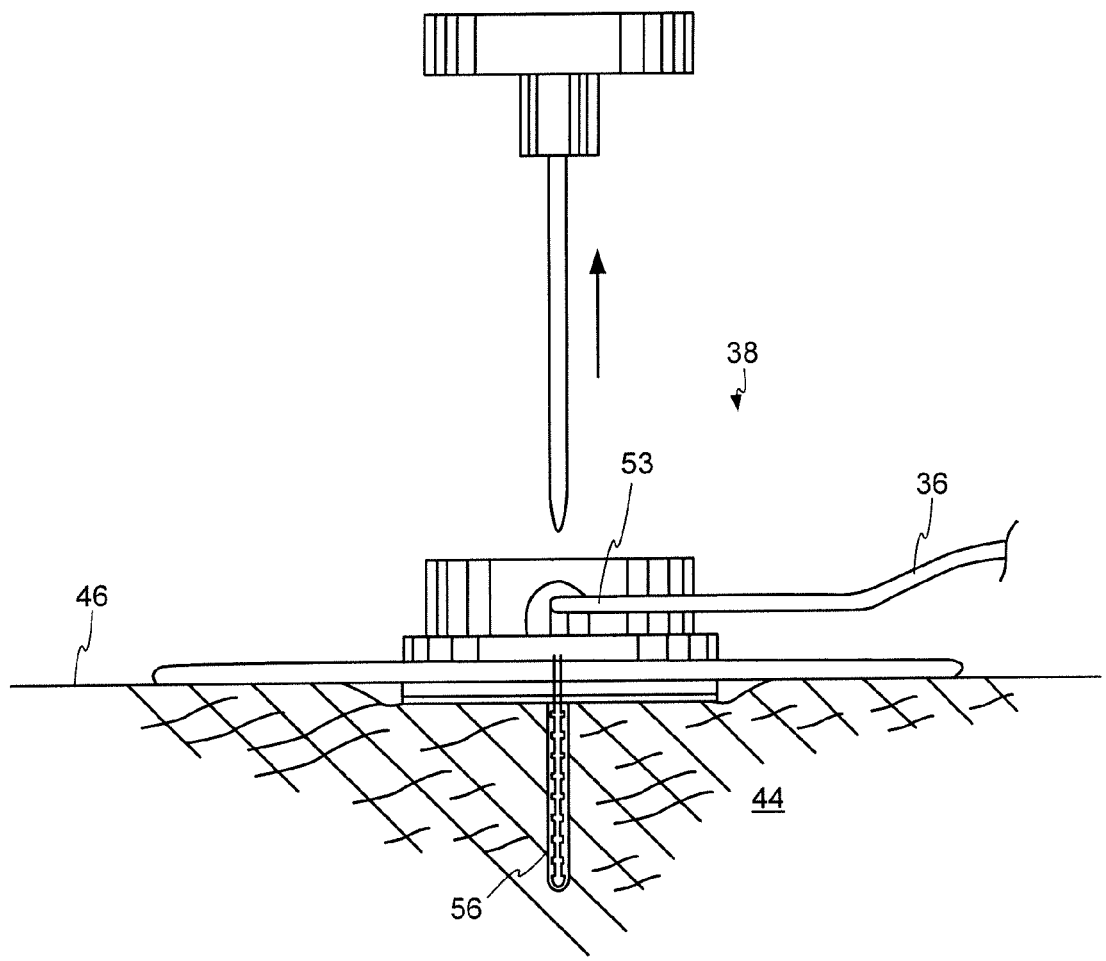
FIG. 6 is a side view of an example infusion set with an insertion needle pulled out, for use according to an embodiment.

FIGS. 2-6 illustrate example glucose control systems in accordance with certain embodiments. FIG. 2 is a front view of example closed loop hardware located on a body in accordance with certain embodiments. FIGS. 3(a)-3(d) and 4 show different views and portions of an example glucose sensor system for use in accordance with certain embodiments. FIG. 5 is a top view of an example infusion device with a reservoir door in an open position in accordance with certain embodiments. FIG. 6 is a side view of an example infusion set with an insertion needle pulled out in accordance with certain embodiments.

Particular example embodiments may include a sensor 26, a sensor set 28, a telemetered characteristic monitor 30, a sensor cable 32, an infusion device 34, an infusion tube 36, and an infusion set 38, any or all of which may be worn on a body 20 of a user or patient, as shown in FIG. 2. As shown in FIGS. 3(a) and 3(b), telemetered characteristic monitor 30 may include a monitor housing 31 that supports a printed circuit board 33, battery or batteries 35, antenna (not shown), a sensor cable connector (not shown), and so forth. A sensing end 40 of sensor 26 may have exposed electrodes 42 that may be inserted through skin 46 into a subcutaneous tissue 44 of a user's body 20, as shown in FIGS. 3(d) and 4. Electrodes 42 may be in contact with interstitial fluid (ISF) that is usually present throughout subcutaneous tissue 44.

Sensor 26 may be held in place by sensor set 28, which may be adhesively secured to a user's skin 46, as shown in FIGS. 3(c) and 3(d). Sensor set 28 may provide for a connector end 27 of sensor 26 to connect to a first end 29 of sensor cable 32. A second end 37 of sensor cable 32 may connect to monitor housing 31. Batteries 35 that may be included in monitor housing 31 provide power for sensor 26 and electrical components 39 on printed circuit board 33. Electrical components 39 may sample sensor signal 16 (e.g., of FIG. 1) and store digital sensor values (Dsig) in a memory. Digital sensor values Dsig may be periodically transmitted from a memory to controller 12, which may be included in an infusion device.

With reference to FIGS. 2 and 5 (and FIG. 1), a controller 12 may process digital sensor values Dsig and generate commands 22 (e.g., of FIG. 1) for infusion device 34. Infusion device 34 may respond to commands 22 and actuate a plunger 48 that forces insulin 24 (e.g., of FIG. 1) out of a reservoir 50 that is located inside an infusion device 34. Glucose may be infused from a reservoir responsive to commands 22 using a similar and/or analogous device (not shown). In alternative implementations, glucose may be administered to a patient orally.

In particular example embodiments, a connector tip 54 of reservoir 50 may extend through infusion device housing 52, and a first end 51 of infusion tube 36 may be attached to connector tip 54. A second end 53 of infusion tube 36 may connect to infusion set 38 (e.g., of FIGS. 2 and 6). With reference to FIG. 6 (and FIG. 1), insulin 24 (e.g., of FIG. 1) may be forced through infusion tube 36 into infusion set 38 and into body 16 (e.g., of FIG. 1). Infusion set 38 may be adhesively attached to a user's skin 46. As part of infusion set 38, a cannula 56 may extend through skin 46 and terminate in subcutaneous tissue 44 to complete fluid communication between a reservoir 50 (e.g., of FIG. 5) and subcutaneous tissue 44 of a user's body 16.

In example alternative embodiments, as pointed out above, a closed-loop system in particular implementations may be a part of a hospital-based glucose management system. Given that insulin therapy during intensive care has been shown to dramatically improve wound healing and reduce blood stream infections, renal failure, and polyneuropathy mortality, irrespective of whether subjects previously had diabetes (See, e.g., Van den Berghe G. et al. NEJM 345: 1359-67, 2001), particular example implementations may be used in a hospital setting to control a blood glucose level of a patient in intensive care. In such alternative embodiments, because an intravenous (IV) hookup may be implanted into a patient's arm while the patient is in an intensive care setting (e.g., ICU), a closed loop glucose control may be established that piggy-backs off an existing IV connection. Thus, in a hospital or other medical-facility based system, IV catheters that are directly connected to a patient's vascular system for purposes of quickly delivering IV fluids, may also be used to facilitate blood sampling and direct infusion of substances (e.g., insulin, glucose, anticoagulants, etc.) into an intra-vascular space.

Moreover, glucose sensors may be inserted through an IV line to provide, e.g., real-time glucose levels from the blood stream. Therefore, depending on a type of hospital or other medical-facility based system, such alternative embodiments may not necessarily utilize all of the described system components. Examples of components that may be omitted include, but are not limited to, sensor 26, sensor set 28, telemetered characteristic monitor 30, sensor cable 32, infusion tube 36, infusion set 38, and so forth. Instead, standard blood glucose meters and/or vascular glucose sensors, such as those described in co-pending U.S. Patent Application Publication No. 2008/0221509 (U.S. patent application Ser. No. 12/121,647; to Gottlieb, Rebecca et al.; entitled "MULTILUMEN CATHETER"), filed 15 May 2008, may be used to provide blood glucose values to an infusion pump control, and an existing IV connection may be used to administer insulin to an patient. Other alternative embodiments may also include fewer, more, and/or different components than those that are described herein and/or illustrated in the accompanying Drawings.

In particular example embodiments, a sensor system may generate a message that includes information based on a sensor signal such as digital sensor values, pre-filtered digital sensor values, filtered digital sensor values, calibrated digital sensor values, commands, and so forth, just to name a few examples. Such a message may include other types of information as well, including, by way of example but not limitation, a serial number, an ID code, a check value, values for other sensed parameters, diagnostic signals, other signals, and so forth. In particular example embodiments, digital sensor values Dsig may be filtered in a telemetered characteristic monitor transmitter 30, and filtered digital sensor values may be included in a message sent to infusion device 34 where the filtered digital sensor values may be calibrated and used in a controller. In other example embodiments, digital sensor values Dsig may be filtered and calibrated before transmission to a controller in infusion device 34. Alternatively, digital sensor values Dsig may be filtered, calibrated, and used in a controller to generate commands 22 that are sent from telemetered characteristic monitor transmitter 30 to infusion device 34.

In further example embodiments, additional components, such as a post-calibration filter, a display, a recorder, a blood glucose meter, etc. may be included in devices with any of the other components, or they may stand-alone. If a blood glucose meter is built into a device, for instance, it may be co-located in the same device that contains a calibrator.

Example Applications of Sensor Reliability Indicator and/or Metric

As pointed out above, a metric and/or indicator representing a sensor's ability to provide signals to accurately represent blood glucose measurements may have any one of several applications. It should be understood, however, that these are merely example applications and not intended to be an exhaustive enumeration of such applications, and that claimed subject matter is not limited in this respect.

In one particular implementation, blood glucose concentration measurements are obtained according to a mapping of sensor signal values to blood glucose sensor measurements. Such a mapping may be derived and/or updated based, at least in part, on temporally correlated pairs of blood glucose reference samples and sensor sample values according to a "calibration process." Examples of such a calibration process may be performed according to U.S. patent application Ser. No. 12/345,477, filed on Dec. 29, 2008 or U.S. patent application Ser. No. 13/239,265, filed on Sep. 21, 2011, incorporated herein by reference in their entirety. In a particular implementation, a calibration cycle may be performed from time to time using a newly obtained metered blood glucose reference sample that is temporally correlated with a sensor sample value in a pair as discussed above. Using the newly obtained pair, a calibration process may provide updated parameters mapping sensor signal values to blood glucose concentration measurements.

In one particular implementation, controller 12 may determine times that a patient is to provide a blood-glucose reference sample for use in a calibration process for obtaining updated parameters mapping sensor signal values to blood glucose concentration measurements. In one example, an alert signal may be provided to a patient and/or hospital attendant requesting a new blood-glucose reference sample. Such an alert signal may be generated at predetermined intervals. However, in a particular implementation, the time between such alert signals for requesting blood-glucose reference samples may be varied based, at least in part, on a metric and/or indicator of reliability of a sensor as mentioned above. Here, for example, if such a metric and/or indicator suggests that a sensor's signals represent a blood glucose concentration relatively accurately, intervals between blood-glucose reference samples may be lengthened. Likewise, if such a metric and/or indicator suggests that a sensor's signals represent a blood glucose concentration relatively inaccurately, intervals between blood-glucose reference samples may be shortened.

In another example embodiment, a metric and/or indicator may be used to provide an indication on a display to indicate a degree of reliability associated with an ability of the sensor to provide accurate measurements of blood-glucose concentration. Such an indication may be provided, for example, on a display (e.g., on controller 12 or monitor 30). Here, such a display could be a number on a scale (e.g., from 0.0 to 10.0), a light to indicate good, fair, bad or defective, bars, just to name a few of examples of how a degree of reliability of a sensor in providing signals that accurately represent a blood-glucose concentration in a patient.

In a hospital application, a caretaker or attendant may be tasked to make periodic rounds to take metered blood glucose reference samples for determining insulin dosing. These blood glucose reference samples may also be used to calibrate a blood glucose sensor to provide signals representing a blood glucose concentration in the patient according to a continuous blood glucose monitoring scheme. In one scenario, an estimated blood glucose concentration of a patient based upon blood glucose measurements obtained from a glucose sensor may be determined to be within a target glucose level for a patient. Here, if an associated metric and/or indicator indicates that the sensor is providing measurements with sufficient accuracy reliably, incorporation of metered blood glucose reference samples may be delayed, suspended or obtained at longer intervals as illustrated with specific examples in U.S. patent application Ser. No. 13/171,244, filed on Jun. 28, 2011, and incorporated herein by reference.

As discussed elsewhere herein according to particular embodiments, a closed loop insulin infusion system may rely on blood glucose concentration measurements obtained from a blood glucose sensor. Here, providing an appropriate dose of insulin and/or glucagon may rely on the accuracy of measurements of blood glucose concentration. In one example implementation, an indicator and/or metric representing a degree of reliability associated with an ability of the sensor to provide accurate measurements of blood-glucose concentration may be used to determine whether closed loop operation may continue, or whether manual or open-loop operation is to commence. For example, such a metric and/or indicator may be expressed as a numerical value which is applied to a threshold to determine whether the sensor is operating sufficiently reliably to continue closed-loop operation, or whether manual or open-loop operation is to commence. Here, application of the metric and/or indicator to the threshold may generate a control signal to at least in part initiate a transition to open-loop or manual operation.

As discussed elsewhere herein, a glucose sensor may have a limited operational life after which the glucose sensor may be replaced with a new glucose sensor. In certain implementations, such an operational life may be terminated at a set duration or period. Alternatively, such an operational life may be terminated based upon a detection of a fault or malfunction. In a particular implementation, an operational life of a blood glucose sensor may be extended by taking into consideration a reliability metric and/or indicator as described herein. Here, for example, the operational life of a glucose sensor may be extended beyond any particular set duration or period if the metric and/or indicator indicates that the sensor is likely providing signals that represent a patient's blood glucose concentration with sufficient accuracy. In an alternative implementation, such a metric and/or indicator may be used to prompt or request additional or more frequent metered blood reference samples for use in calibration as discussed above. By calibrating the sensor more often and/or with a greater number of metered blood glucose reference samples, the operational life of a glucose sensor may be extended beyond a set duration or period.

FIGS. 7 through 17 are directed to a particular implementation that includes a sensor module for application to a patient where the sensor module includes four glucose sensors comprising a pair of glucose sensors forming a left probe 504 and a pair of sensors forming a right probe 502. Here, these blood glucose sensors forming right probe 502 and left probe 504 may be capable of providing four associated signal values representing and/or responding to a blood glucose concentration in a patient. At FIG. 7, a sensor module including four sensors is connected to a processor that performs signal condition and filtering operations, for example. Coupled to processor 506 is monitor 508 that includes a tight glucose control (TGC) module, an integrity, calibration and fusion (ICF) module, control logic and a graphical user interface (GUI). In a particular application, the ICF module may determine a reliability index (RI) which may provide or relate to a metric and/or indicator representative of an ability to provide sensor signal representative of blood-glucose concentration with sufficient accuracy for a particular application.

Figure 8:
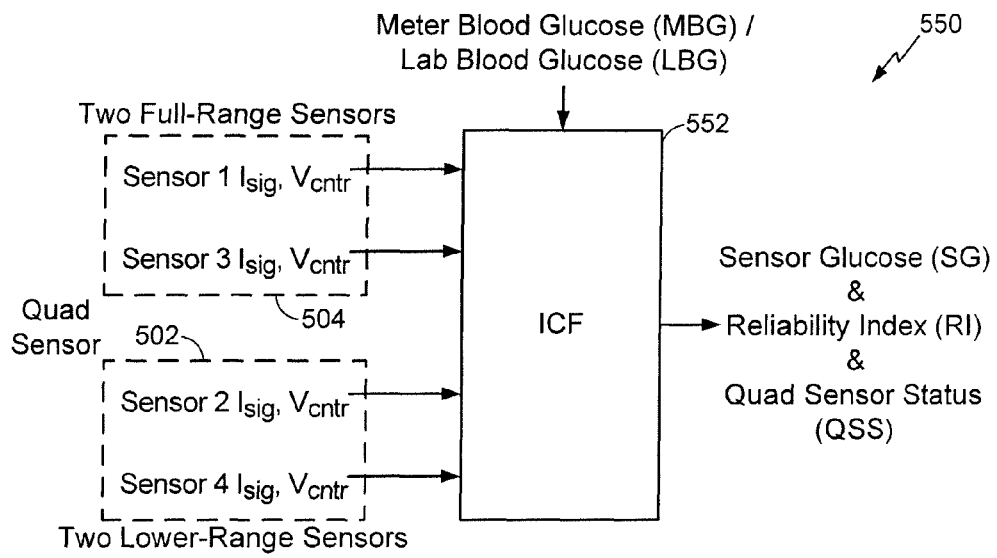

As shown in FIG. 8, an ICF module 552 receives from each of four sensors a value ISIG, which may be a current signal representative of and/or responsive to a presence of glucose in fluid (e.g., interstitial fluid), and $V_{counter}$, which may represent a voltage between or among electrodes of a sensor and used to diagnose health of the sensor. Here, in a particular implementation, $V_{counter}$ may be indicative of an amount of power being consumed to generate a suitable current for ISIG values. An abnormally high value for $V_{counter}$ may be indicative of a decrease in sensitivity or dynamic range in responding to a presence of glucose in interstitial fluid. Right probe 502 may comprise a pair of sensors directed to providing measurements of glucose concentration in a lower range while left probe 504 may be direct to providing measurements of glucose concentration in a full range. ICF module 552 receives reference blood glucose samples from a patient such as metered blood glucose samples or lab blood glucose samples for use in calibration of sensors as discussed above. ICF module 552 may produce a sensor glucose measurement SG, which may represent a patient's blood glucose concentration level, a reliability index as discussed above, and a quad sensor status (QSS) signal. In a particular implementation, QSS may have values or states including, for example, "pending," "good," "bad" or "failed." SG may comprise a numerical value in a range of ~40.0 to 400 mg/dl. In one particular implementation, RI may be expressed as a numerical value (e.g., from 0.0 to 1.0) and may be determined periodically (e.g., once per minute). QSS may provide a status indication such as, for example, pending, good, bad or failed.

FIG. 9 illustrates an integrity check and calibration that is performed in a particular implementation of an IFC (e.g., ICF 552 shown in FIG. 8) that is performed for each sensor in a sensor module. Here, for each sensor an integrity check is performed to evaluate reliability internally (e.g., using hardware status checks, trend analysis, noise analysis), followed by a calibration scheme to update or determine a function mapping values for ISIG to blood glucose concentration measurements. At this point, and as elaborated below, a correlation between or among ISIG sensor signal values is computed for combinations of sensor pairs in the sensor module. Processed values for ISIG from four channels may then be fused at a sensor fusion module to provide values for SG, RI and QSS.

Figure 10:
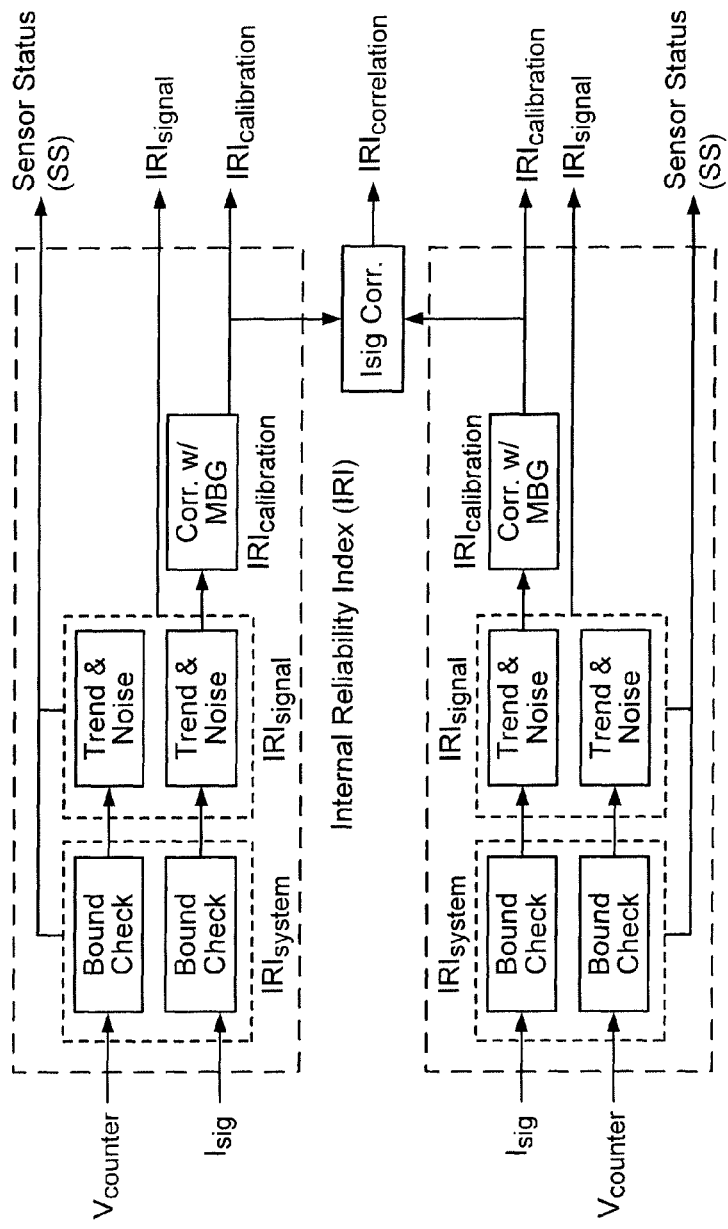

FIG. 10 illustrates a technique for performing an integrity check according to a particular implementation of an integrity check shown in FIG. 9. For each sensor channel, a bound check is performed for respective $V_{counter}$ and ISIG values to provide value $IRI_{system}$ as described below in a specific implementation according to FIG. 13. Also, trend and noise analysis may generate value $IRI_{signal}$ using any one of several techniques as described below. Here, past sensor behavior may be evaluated to identify any observed trends consistent with a loss of reliability of a sensor to provide sufficiently accurate measurements of glucose concentration and/or sensitivity of the sensor in responding to the presence of glucose. Such an observed trend may comprise, for example, an observed change in sensitivity of the blood glucose sensor; at least one observed non-physiological anomaly; or an observed sensor drift as described in U.S. patent application Ser. No. 12/820,944, filed on Jun. 22, 2010, and Ser. No. 12/914,963, filed on Oct. 27, 2010, and U.S. Provisional Patent Application Ser. No. 61/407,884 filed on Oct. 28, 2010, which are assigned to the assignee of claimed subject matter and incorporated by reference herein in their entirety.

Figure 11:
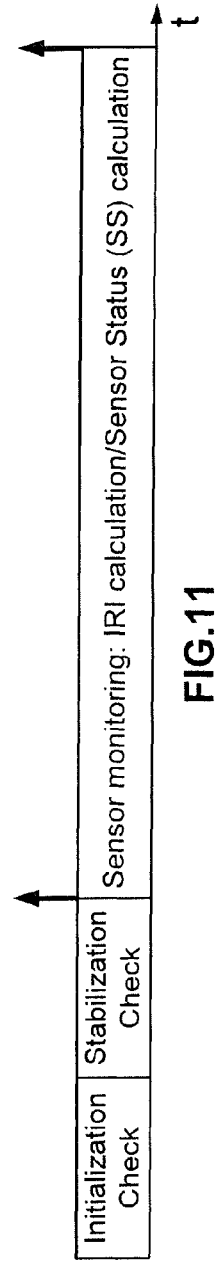
Figure 12:
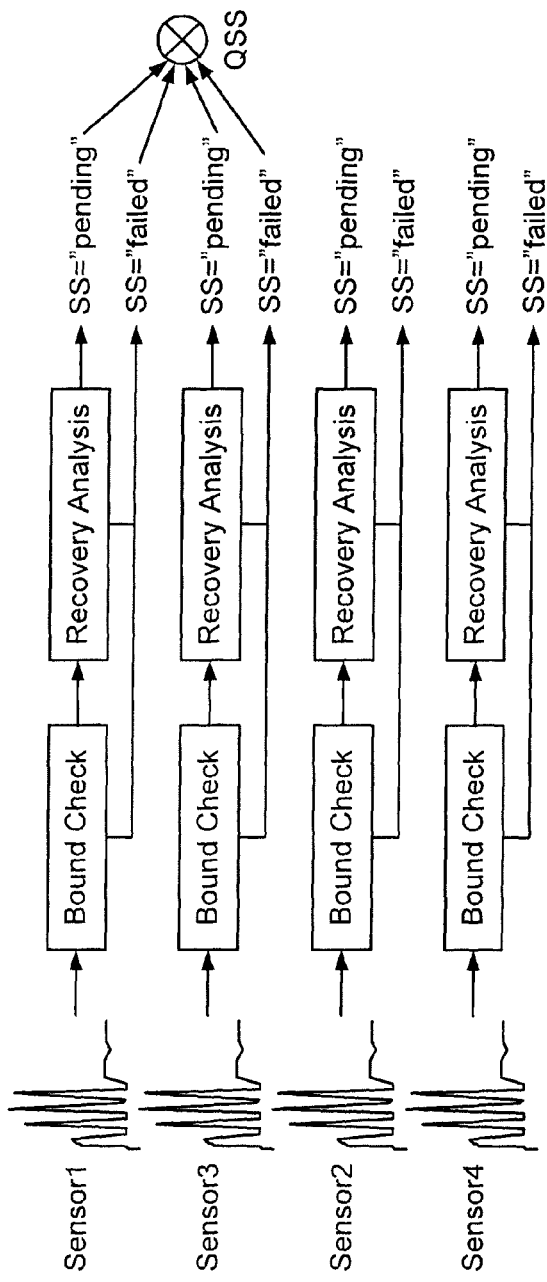

In a particular implementation, prior to use of a sensor a process as illustrated in the timeline of FIG. 11 may be performed whereby an initialization check is followed by a stabilization check. Here, a sensor may be provided a series of pulses to remove electrons followed by an evaluation of an output signal to confirm proper recovery of the sensor as shown in FIG. 12. Sensor monitoring to determine sensor reliability and status may commence.

Figure 13:
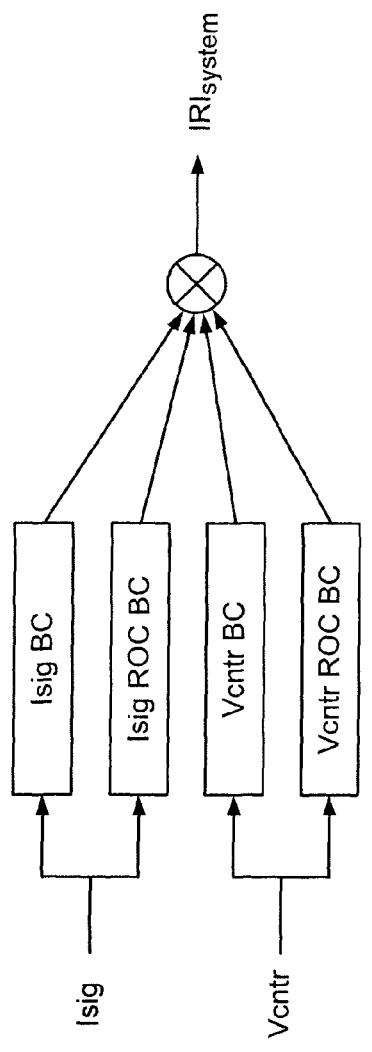

FIG. 13 shows an implementation of a bound check for determining a value $IRI_{system}$ as indentified above with reference to FIG. 10. $IRI_{system}$ may indicate, for example, a reliability of sensor hardware. Here, a bound check is applied to values for ISIG, $V_{counter}$, rates of change for ISIG and $V_{counter}$ to provide a value such as a value of 0.0, 0.5 or 1.0 in a particular implementation. For example, if values for ISIG and $V_{counter}$ are within expected ranges, a value 1.0 may be assigned. If a value is outside of any expected operational bound, a value of 0.0 may be assigned. If a value is within an operational bound but at a reduced confidence level, a value of 0.5 may be assigned. A minimum of the assigned values may then be selected as the value $IRI_{system}$. Of course these are merely examples of how a numerical value may be assigned to a metric indicative of reliability and claimed subject matter is not limited in this respect.

Figure 14:
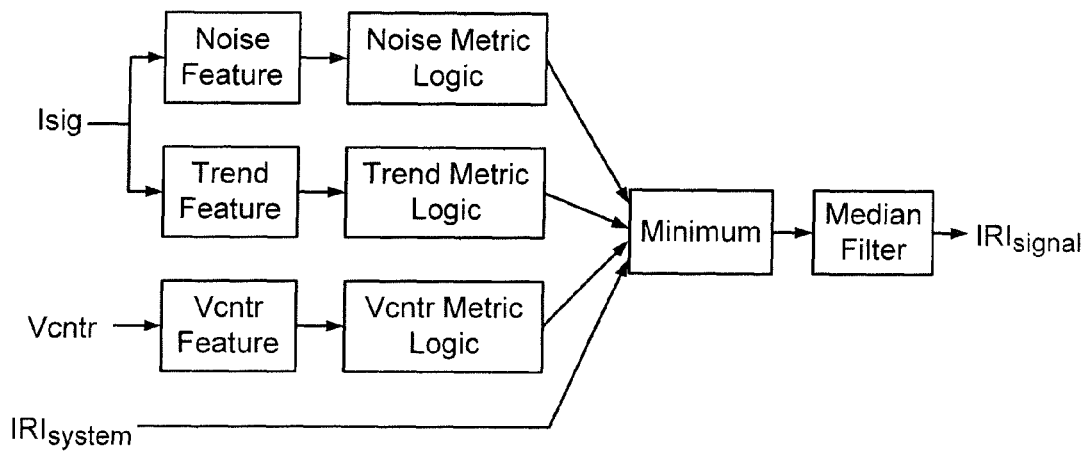

FIG. 14 shows an implementation of noise and trend analysis identified in FIG. 10 to provide a value $IRI_{signal}$. Regarding analysis of an ISIG signal, a signal trend feature analysis may include characterizing a long-term, non-physiological trend, a sensor that is losing sensitivity, and/or a sensor that is operating outside of expected operation bounds. Specific non-limiting examples of trend feature analysis are provided in the aforementioned U.S. patent application Ser. Nos. 12/820,944 and 12/914,963, and U.S. Provisional Patent Application Ser. No. 61/407,884. A noise feature analysis may characterize the presence of noise in connection with ISIG values in real-time. Also, an analysis of $V_{counter}$ may detect features such as virtual rail and swing and/or other signs of instability. In a particular implementation, noise metric logic, trend metric logic and $V_{counter}$ metric logic may each provide a numerical value (e.g., a continuous value ranging from 0.0 to 1.0). A minimum value of values representing a noise metric, trend metric, $V_{counter}$ metric and IRI_system may be selected as a value, which is applied to a temporal filter over a time period to produce $IRI_{signal}$.

A noise metric may be computed using any one of several techniques including, for example, signal decomposition (e.g., wavelet, empirical mode decomposition) may be used to decompose ISIG into signal and noise. The power of the noise and signal may then be used for computing a noise level.

In another example technique, a noise metric may be computed by application of a low pass filter such as finite impulse response (FIR) filters (including Savitzky-Golay filters), infinite impulse response (IIR) filters may be applied to values of ISIG. A difference between a filtered and unfiltered signal may be considered as an indicator of a noise level.

In another example technique, a noise metric may be computed based, at least in part, on application of singular spectral analysis (SSA) to estimate ISIG noise level. Here, a lag-covariance matrix of ISIG may be constructed based on a raw signal. A noise level may then be estimated through eigen analysis of the lag-covariance matrix.

In another example technique, a noise metric MetNoise may be computed as follows:

MetNoise=($TH\_NOISE2-isignoise$)/($TH\_NOISE2-TH\_NOISE1$), where:

isignoise=abs(Isig(n)−2×Isig(n−1)+Isig(n−2)); and

Isig(k) is a value of an ISIG signal from a sensor sampled at time k.

Values for TH_NOISE1 and TH_NOISE2 may set hard thresholds for a noise level. If the estimated noise level isignoise is exceeds upper threshold TH_NOISE2, MetNoise may be set to 0. If the estimated noise level isignoise does not exceed lower threshold TH_NOISE1, MetNoise may be set to 1. Accordingly, a numerical range of MetNoise may be set to a value within [0,1] for this particular embodiment.

$V_{counter}$ metric logic may determine a metric for estimating a long-term rate of change within a period that indicates that a sensor is not stable. Here, a large swing in the value $V_{counter}$ for a sensor may indicate that the sensor is not stable. A large swing in the value $V_{counter}$ may be detected over a time window in the past. A metric for detecting $V_{counter}$ rate of change over a time interval may be expressed as follows:

$$MetVcntr = k1 - (mean(V_{roc})/k2 + V_{counter}(n)/k3)/2,$$

Where:

k1, k2, k3 are chosen so that the MetVcntr will fall in the numerical range of [0, 1].

Figure 7:
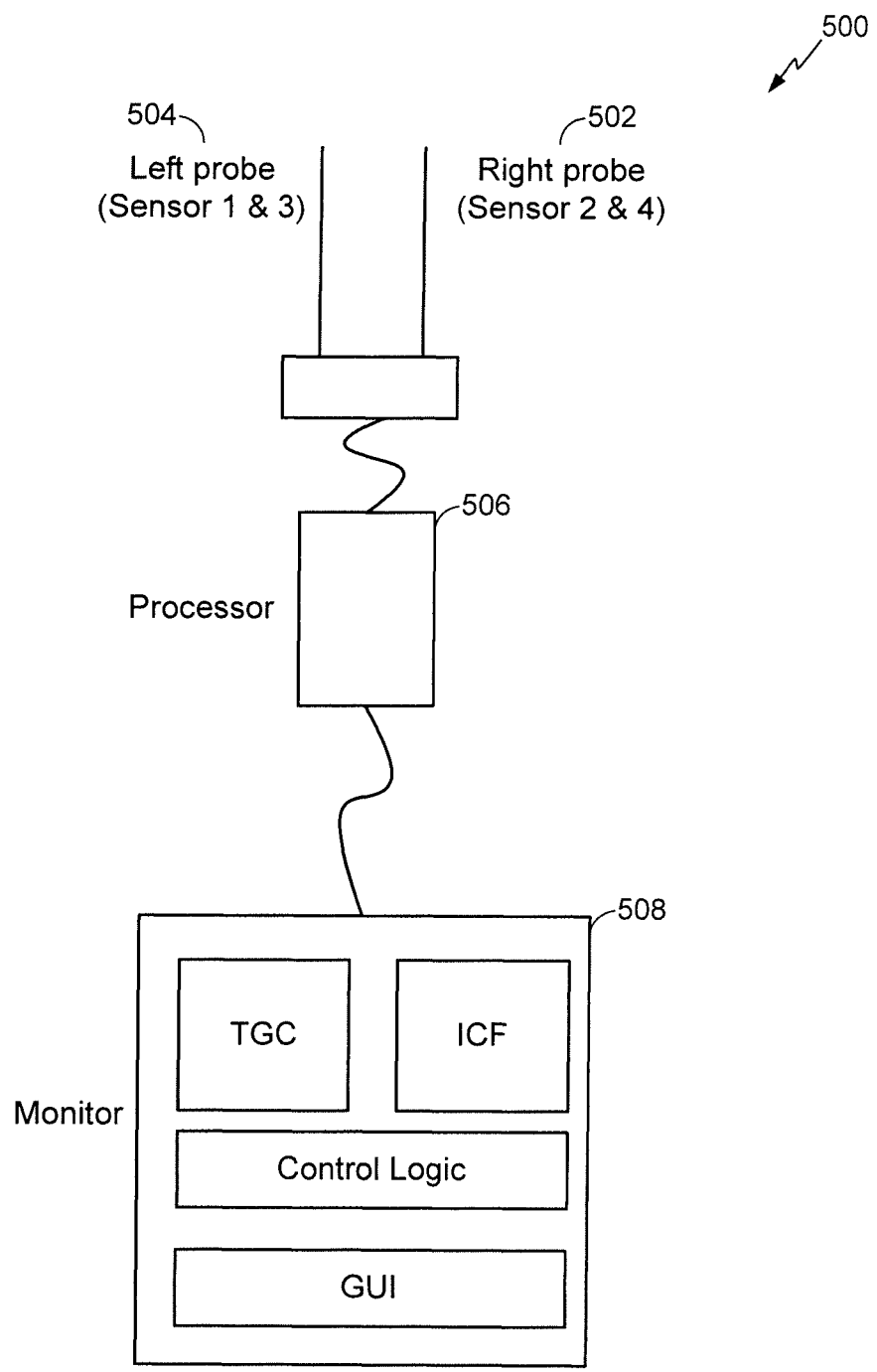
FIGS. 7 through 17 are directed to apparatuses and techniques for determining a metric and/or indicator representative of a reliability of a sensor to provide measurements of sufficient accuracy for an application according to an embodiment.
Figure 15:
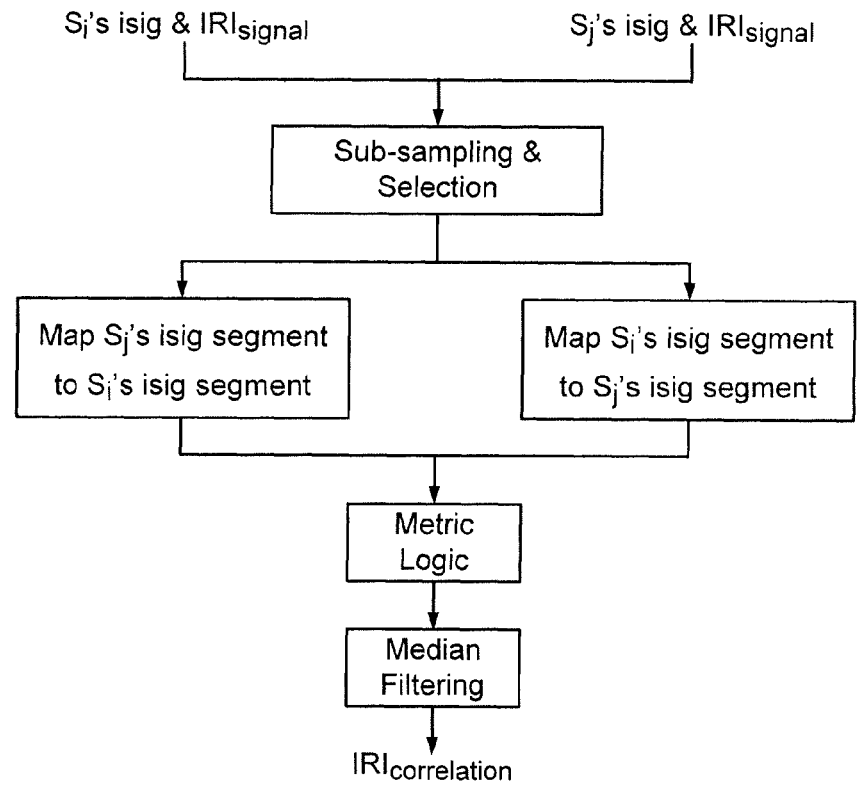
Figure 16:
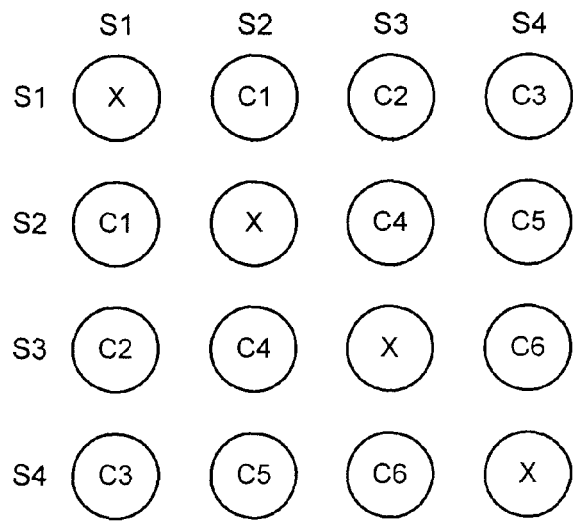

FIGS. 15 and 16 are directed to a technique for generating a value $IRI_{correlation}$ representing a cross correlation of values for ISIG and $IRI_{signal}$ for a sensor obtained at regular intervals such as sample intervals. Here, a value for $IRI_{correlation}$ may be assigned between at 0.0 and 1.0 for each pair of sensors. As in the particular embodiment with a sensor module having four sensors as shown in FIG. 7, there would be six pairings of sensors with corresponding correlation values C1, C2, C3, C4, C5 and C6 as shown in FIG. 16. In a particular implementation, only pairs of signal samples with both IRI_signal greater than a threshold may be chosen for computing a correlation metric. For any particular pair of sensor elements, two arrays Isig1 and Isig2, with elements an array corresponding with a sensor element for a series of ISIG values obtained from the sensor element. For different elements i and j in the arrays Isig1 and Isig2, a value for s (i,j) may be computed as follows:

$$s(i,j) = [Isig1(i) - Isig1(j)]/[Isig2(i) - Isig2(j)].$$

Values for s(i,j) for any particular sensor pair may be used for computing a linear mapping between the two sensor elements defined by a slope value and an intercept value. Values for s(i,j) less than zero may be ignored. In one particular implementation, the slope value ("slope") may be determined as a median value of s (i,j) while the intercept value may be set to the median of Isig1(i)–slope×Isig2(i) over i. Based upon this linear mapping two residual values res21 and res12 may be obtained. Here, a metric for assessing correlation between two sensor elements for a specific sampling time n may be determined as follows:

$$MetCorrelation = 1 - (res21 + res12)/(Isig1(n) + Isig2(n))$$

With four sensor elements, up to six values for MetCorrelation may be determined for a time n. The value for IRI_correlation may be determined as a mean value for MetCorrelation among multiple pairs of sensors.

In a particular implementation, ISIG values may be applied to a function that maps sensor signal values to sensor measurements of blood glucose concentration. In one particular implementation, such a function is provided as a linear function defined by a $sl_{ope\ or\ rate}$ and an offset value which are updated from time to time using a calibration process. According to an embodiment, the value $IRI_{calibration}$ for a particular sensor channel may be obtained an application based upon a calculation of a slope m as follows:

$$m = MBG(t)/ISIG(t+T),$$

where:

MBG(t) is a metered blood glucose reference sample value obtained at time t; and ISIG(t+T) is a sensor signal value obtained at time t+T.

The slope m may then be applied to a threshold to determine a value for $IRI_{calibration}$ between 0.0 and 1.0.

Figure 17:
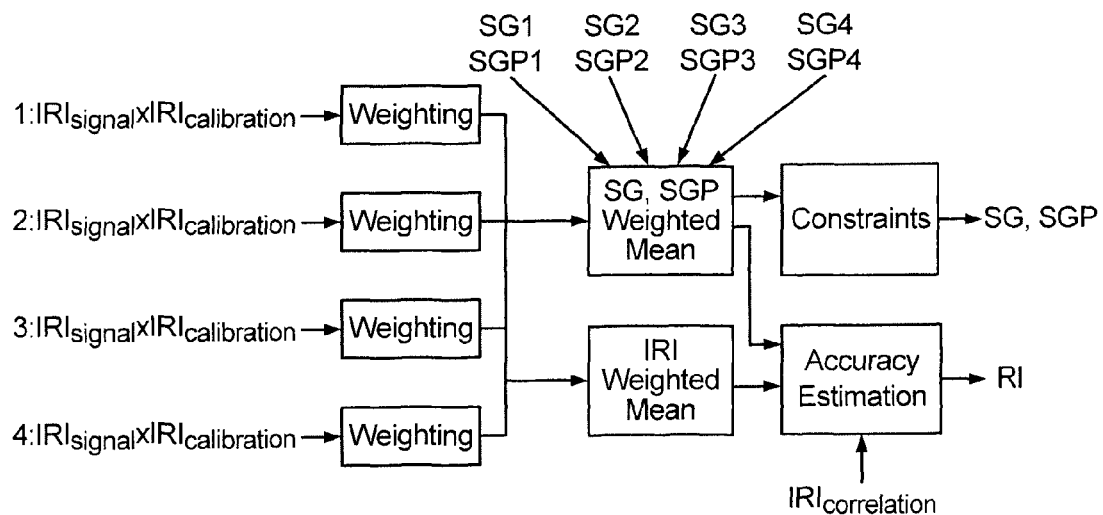

FIG. 17 illustrates a process for fusing measurements and signals from multiple sensors in a sensor module for obtaining sensor blood glucose concentration measurements and a reliability indicator RI. Here, for each sensor in a sensor module a weighting may be computed based, at least in part, on a combination of corresponding values $IRI_{signal}$ and $IRI_{calibration}$. Such a weighting may be applied to associated glucose sensor measurements SG1, SG2, SG3 and SG4 to produce a single blood glucose sensor measurement, and applied to associated predicted glucose sensor measurements SGP1, SGP2, SGP3 and SGP4 to produce a single predicted glucose sensor measurement SGP. In a particular implementation, such a weighting $W_i$ to be applied may be computed as follows:

$$W_i = -\frac{1}{\log(IRI\_signal_i \times IRI\_calibration_i + c)}$$

Where:

IRI_signal, is a value $IRI_{signal}$, for sensor channel i;

IRI_calibration, is a value $IRI_{calibration}$ for sensor channel i; and c is a constant.

Optionally, if there is at least one past blood glucose reference value used for calibrating sensor i, a weight $W_i$ may be computed as follows:

$$W_i = -\frac{1}{\log(IRI\_signal_i \times IRI\_calibration_i \times (1 - ARD_i) + c)}$$

where $ARD_i$ is a mean absolute relative difference computed as follows:

$$ARD_i = \frac{|BG_i - SG_i|}{SG_i},$$

Where $BG_i$ is a blood glucose reference sample value obtained at time i.

In one embodiment, a value for $IRI\_signal_i \times IRI\_calibration$, for a particular sensor i exceeds a threshold value before measurements obtained from sensor i may be incorporated into a sensor blood glucose measurement obtained from fusing measurements from multiple sensors.

A sensor glucose value at a time n fused from the four elements may be computed as follows:

$$SG(n) = \frac{\sum_i W_n^i \times SG_n^i}{\sum_i W_n^i}$$

for sensor elements i=1, 2, 3 and 4 in the particular illustrated embodiment.

In addition to application of weights $W_i$ to glucose sensor measurements and predicted glucose sensor measurements, weights $W_i$ may also be applied in determining RI. A value for RI may be computed based, at least in part, on the aforementioned value for $ARD_i$ as follows:

$$RI(n) = 1 - ArdRef(n) \times \left(1 - \frac{FRI(n) - RIRef(n)}{RIRef(n)}\right)$$

First, a reference ARD, ArdRef, for a current point n may be computed as follows:

$$ArdRef(n) = \frac{\sum_i u_i \times ARD_i}{\sum_i u_i}$$

Where: $u_i 1 - IRI\_correlation(i)$

A reference reliability index RIRef for a current point n may be computed as follows:

$$RIRef(n) = \frac{\sum_i u_i \times FRI_i}{\sum_i u_i}$$

The IRIS ($IRI_{signal} \times IRI_{calibration}$) may be processed to determine a weighted mean according to values for $W_i$ to yield a middle value FRI which may be computed as follows:

$$FRI(n) = \frac{\sum_i W_n^i \times IRI_{system_n}^i \times IRI_{calibration_n}^i}{\sum_i W_n^i}$$

Unless specifically stated otherwise, as is apparent from the preceding discussion, it is to be appreciated that throughout this specification discussions utilizing terms such as "processing", "computing", "calculating", "determining", "assessing", "estimating", "identifying", "obtaining", "representing", "receiving", "transmitting", "storing", "analyzing", "measuring", "detecting", "controlling", "delaying", "initiating", "providing", "performing", "generating", "altering" and so forth may refer to actions, processes, etc. that may be partially or fully performed by a specific apparatus, such as a special purpose computer, special purpose computing apparatus, a similar special purpose electronic computing device, and so forth, just to name a few examples. In the context of this specification, therefore, a special purpose computer or a similar special purpose electronic computing device may be capable of manipulating or transforming signals, which are typically represented as physical electronic and/or magnetic quantities within memories, registers, or other information storage devices; transmission devices; display devices of a special purpose computer; or similar special purpose electronic computing device; and so forth, just to name a few examples. In particular example embodiments, such a special purpose computer or similar may comprise one or more processors programmed with instructions to perform one or more specific functions. Accordingly, a special purpose computer may refer to a system or a device that includes an ability to process or store data in the form of signals. Further, unless specifically stated otherwise, a process or method as described herein, with reference to flow diagrams or otherwise, may also be executed or controlled, in whole or in part, by a special purpose computer.

It should be understood that aspects described above are examples only and that embodiments may differ there from without departing from claimed subject matter. Also, it should be noted that although aspects of the above systems, methods, apparatuses, devices, processes, etc. have been described in particular orders and in particular arrangements, such specific orders and arrangements are merely examples and claimed subject matter is not limited to the orders and arrangements as described. It should additionally be noted that systems, devices, methods, apparatuses, processes, etc. described herein may be capable of being performed by one or more computing platforms.

In addition, instructions that are adapted to realize methods, processes, etc. that are described herein may be capable of being stored on a storage medium as one or more machine readable instructions. If executed, machine readable instructions may enable a computing platform to perform one or more actions. "Storage medium" as referred to herein may relate to media capable of storing information or instructions which may be operated on, or executed by, one or more machines (e.g., that include at least one processor). For example, a storage medium may comprise one or more storage articles and/or devices for storing machine-readable instructions or information. Such storage articles and/or devices may comprise any one of several media types including, for example, magnetic, optical, semiconductor, a combination thereof, etc. storage media. By way of further example, one or more computing platforms may be adapted to perform one or more processes, methods, etc. in accordance with claimed subject matter, such as methods, processes, etc. that are described herein. However, these are merely examples relating to a storage medium and a computing platform and claimed subject matter is not limited in these respects.

Although there have been illustrated and described what are presently considered to be example features, it will be understood by those skilled in the art that various other modifications may be made, and equivalents may be substituted, without departing from claimed subject matter. Additionally, many modifications may be made to adapt a particular situation to the teachings of claimed subject matter without departing from central concepts that are described herein. Therefore, it is intended that claimed subject matter not be limited to particular examples disclosed, but that such claimed subject matter may also include all aspects falling within the scope of appended claims, and equivalents thereof.

What is claimed is:

1. A method comprising:
    determining an indicator of reliability of a blood glucose sensor, the blood glucose sensor comprising at least a first probe and a second probe, the first and second probes comprising two or more pairs of sensor elements, the indicator of reliability of the blood glucose sensor being based, at least in part, on an observed correlation of output signals generated by at least a first pair of the pairs of sensor elements; and
    generating a signal to suggest replacement of the blood glucose sensor based, at least in part, on the indicator of reliability of the blood glucose sensor.

2. The method of claim 1, wherein the indicator of reliability of the blood glucose sensor is further based, at least in part, on an additional observed correlation of output signals generated by at least a second pair of the pairs of sensor elements.

3. The method of claim 1, further comprising displaying an image on a display based, at least in part, on the indicator of reliability.

4. The method of claim 1, wherein the blood glucose sensor is coupled to an insulin pump as part of a system to provide closed-loop continuous insulin infusion to a patient, the method further comprising transitioning the system from closed loop operation to an open loop or manual operation based, at least in part, on the indicator of reliability.

5. The method of claim 1, further comprising displaying an indicator requesting additional or more frequent metered blood glucose reference samples for calibration of the blood glucose sensor in response to the indicator of reliability to thereby extend an operating life of the blood glucose sensor.

6. The method of claim 1, wherein the indicator of reliability is further based, at least in part, on an observed trend in output signals generated by the blood glucose sensor.

7. The method of claim 6, wherein the observed trend comprises detection of a reduced sensitivity of the blood glucose sensor in responding to a presence of glucose.

8. The method of claim 6, wherein the observed trend comprises further comprises one or more detected non-physiological anomalies.

9. The method of claim 6, wherein the observed trend comprises a sensor drift.

10. The method of claim 6, wherein the observed trend comprises a noise trend.

11. The method of claim 1, wherein the indicator of reliability further based, at least in part, on an indicator of a reliability of a calibration of the blood glucose sensor.

12. An apparatus comprising:
a blood glucose sensor to generate signals responsive to a concentration of glucose in a fluid, the blood glucose sensor comprising at least a first probe and a second probe, the first and second probes comprising two or more pairs of sensor elements;
one or more processors to:
determine an indicator of reliability of the blood glucose sensor, the indicator of reliability of the blood glucose sensor being based, at least in part, on an observed correlation of output signals generated by at least a first pair of the pairs of sensor elements; and
generate a signal to suggest replacement of the blood glucose sensor based, at least in part, on the indicator of reliability of the blood glucose sensor.

13. The apparatus of claim 12, wherein the indicator of reliability of the blood glucose sensor is further based, at least in part, on an additional observed correlation of output signals generated by at least a second pair of the pairs of sensor elements.

14. The apparatus of claim 12, further comprising a display device, wherein the one or more processors are further to initiate an image on the display device based, at least in part, on the indicator of reliability.

15. The apparatus of claim 12, further comprising an insulin pump coupled to the blood glucose sensor as part of a system to provide closed-loop continuous insulin infusion to a patient, wherein the one or more processors are further to initiate transition of the system from closed loop operation to an open loop or manual operation based, at least in part, on the indicator of reliability.

16. The apparatus of claim 12, further comprising a display device, wherein the one or more processors are further to initiate an image on the display device, the image requesting additional or more frequent metered blood glucose reference samples for calibration of the blood glucose sensor in response to the indicator of reliability to thereby extend an operating life of the blood glucose sensor.

17. The apparatus of claim 12, wherein the indicator of reliability is further based, at least in part, on an observed trend in the output signals generated by the blood glucose sensor.

18. An article comprising:
a non-transitory storage medium comprising machine-readable instructions stored thereon which are executable by a special purpose computing apparatus to:
determine an indicator of reliability of a blood glucose sensor, the blood glucose sensor comprising at least a first probe and a second probe, the first and second probes comprising two or more pairs of sensor elements, the indicator of reliability of the blood glucose sensor being based, at least in part, on an observed correlation of output signals generated by at least a first pair of the pairs of sensor elements; and
generate a signal to suggest replacement of the blood glucose sensor based, at least in part, on the indicator of reliability of the blood glucose sensor.

19. The article of claim 18, wherein the indicator of reliability of the blood glucose sensor is further based, at least in part, on an additional observed correlation of output signals generated by at least a second pair of the pairs of sensor elements.

20. The article of claim 18, wherein the instructions are further executable by the special purpose computing apparatus to initiate an image on a display device based, at least in part, on the indicator of reliability.

21. The article of claim 18, wherein the instructions are further executable by the special purpose computing apparatus to initiate transition of a system from closed loop operation to an open loop or manual operation based, at least in part, on the indicator of reliability, the system comprising an insulin pump coupled to the blood glucose sensor.

22. The article of claim 18, wherein the instructions are further executable by the special purpose computing apparatus to initiate an image on a display device, the image requesting additional or more frequent metered blood glucose reference samples for calibration of the blood glucose sensor in response to the indicator of reliability to thereby extend an operating life of the blood glucose sensor.

23. The article of claim 18, wherein the indicator of reliability is further based, at least in part, on an observed trend in output signals generated by the blood glucose sensor.

* * * * *